(12) United States Patent
Sugiyama et al.

(10) Patent No.: US 7,360,984 B1
(45) Date of Patent: Apr. 22, 2008

(54) AUTOMATIC ANALYZER AND PART FEEDING DEVICE USED FOR THE ANALYZER

(75) Inventors: Hidetoshi Sugiyama, Hitachinaka (JP); Katsuaki Takahashi, Hitachinaka (JP); Hideyuki Yanami, Hitachinaka (JP); Stephan Sattler, Starnberg (DE)

(73) Assignee: Roche Diagnostics Corp., Indianapolis, IN (US)

( * ) Notice: Subject to any disclaimer, the term of this patent is extended or adjusted under 35 U.S.C. 154(b) by 0 days.

(21) Appl. No.: 10/069,580

(22) PCT Filed: Mar. 15, 2000

(86) PCT No.: PCT/JP00/01574

§ 371 (c)(1),
(2), (4) Date: May 17, 2002

(87) PCT Pub. No.: WO01/69263

PCT Pub. Date: Sep. 20, 2001

(51) Int. Cl.
*B65G 59/08* (2006.01)

(52) U.S. Cl. .................. 414/798.1; 422/63; 422/65

(58) Field of Classification Search .......... 422/63–65, 422/100, 104; 414/798, 798.1, 796.5, 796.7, 414/796.8
See application file for complete search history.

(56) References Cited

U.S. PATENT DOCUMENTS

| | | | | |
|---|---|---|---|---|
| 4,856,073 A | * | 8/1989 | Farber et al. | 382/128 |
| 5,009,316 A | | 4/1991 | Klein | |
| 5,190,434 A | * | 3/1993 | Miura et al. | 414/609 |
| 5,392,914 A | * | 2/1995 | Lemieux et al. | 206/499 |
| 5,827,745 A | * | 10/1998 | Astle | 436/54 |
| 5,882,174 A | * | 3/1999 | Woerner et al. | 414/788.7 |
| 6,143,083 A | * | 11/2000 | Yonemitsu et al. | 118/719 |
| 6,182,719 B1 | * | 2/2001 | Yahiro | 141/130 |

FOREIGN PATENT DOCUMENTS

| | | |
|---|---|---|
| EP | 0654668 | 5/1995 |
| EP | 0937983 | 8/1999 |
| JP | 3002287 | 7/1994 |
| JP | 8-94637 | 4/1996 |
| JP | 8-146010 | 6/1996 |
| JP | 9-33541 | 2/1997 |
| JP | 11-271314 | 10/1999 |
| JP | 11-326341 | 11/1999 |

\* cited by examiner

*Primary Examiner*—Jill Warden
*Assistant Examiner*—Natalia Levkovich
(74) *Attorney, Agent, or Firm*—Mattingly, Stanger, Malur & Brundidge, P.C.

(57) ABSTRACT

An automatic analyzer, comprising disposable parts such as large quantities of nozzle tips and reaction containers for use in sample analysis inspection, wherein the part rack (12) holding unused parts is raised from a lowest position to a rack separation station (A) by a lift for supply (14) and separated so that only the uppermost stacked part rack can remain on the rack separation station, the separated part rack is moved to a part take-out station (B) where parts on the part rack are taken out one by one from a movable holding part (59), and, by opening the floor part of the part take-out station (B) after part consumption, the used part rack is allowed to fall down and recovered on the lift (84) of a recovery lifter (15), whereby the supply of an unused part rack on which unused parts are loaded and the recovery of a used part rack can be performed with a compact system configuration.

6 Claims, 14 Drawing Sheets

AUTOMATIC ANALYZER AND PART FEEDING DEVICE USED FOR THE ANALYZER

TECHNICAL FIELD

The present invention relates to an automatic analyzer using disposable parts used in contact with samples, and a part feeding device for use in the analyzer.

BACKGROUND ART

By treating and measuring living samples such as blood plasma, serum, or urine using various reagents, measured information is obtained which is beneficial for various types of analysis items such as biochemical, immunological, or genetic analysis items. Then, if contamination between the samples must be severely prevented as in the case with the immunological or genetic analysis items, disposable nozzles tips are used. Further, for the same reason, disposable reaction containers may be used to mix the samples and reagents together. By using disposable parts as the nozzle tips and reaction containers, which are brought into contact with the samples, the contamination between the samples or inappropriate inspection data resulting from carryover is reduced.

JP-A-8-146010 specification describes an automatic analyzer using disposable nozzle tips and reaction containers. With this conventional technique, tip racks have a large number of nozzle tips two-dimensionally arranged therein, and vessel racks have a large number of reaction containers two-dimensionally arranged therein. These part racks are so configured to be simply placed in a rack field, and a transportation device takes out nozzle tips or reaction containers from the corresponding rack one by one.

JP-A-8-94637 specification describes a biochemical analyzer comprising an automatic transportation device that transports tip racks in a horizontal direction to a nozzle tip install position and transports used tip racks to a waste preparatory position and then transports the used tip racks to a rack waste position.

JP-A-9-33541 specification describes a tip tray loading device that places a plurality of tip trays in a chute from its top, pulls out the tip trays from the bottom of the chute one by one, transports the pulled-out tip tray to the position of a probe of the automatic analyzer, connects each nozzle tip nozzle to the probe for use, and returns the empty tip tray from which the tips have been consumed, to the bottom of the chute, where the tip trays are dropped and wasted.

DISCLOSURE OF THE INVENTION

With the analyzer described in JP-A-8-146010 specification, it is difficult to automatically sequentially feed disposable parts (nozzle tips and/or reaction containers) required in large quantities, thereby requiring operators to set new tip and vessel racks in a given area and to remove used empty racks from the area. Consequently, this configuration involves temporal restrictions and leaves much room for improvement.

In contrast, the analyzer described in JP-A-8-94637 specification enables a certain level of automation but requires a large space in order to two-dimensionally transport a large number of tip racks. As a result, this analyzer must be generally large in size.

The analyzer described in one more JP-A-9-33541 specification can automatically feed a large number of nozzle tips. However, the operation of separating one tip tray from the others at the bottom of the chute is complicated, so that a take-put trouble is prone to occur in which the tip trays are inappropriately taken out from the chute. Further, since used tip trays are separately dropped and wasted, waste containers must be large in size. Furthermore, the analyzer described in JP-A-9-33541 specification takes out new tip trays only after used tips have been wasted, and thus operates inefficiently. The analyzer described in JP-A-9-33541 specification further requires the tip tray feeding chute to be arranged higher than the position at which each nozzle tip is connected to the probe. Consequently, when the operators performs a certain operation on a sample feeding part, reagent feeding part, or reaction part of the analyzer, the presence of the chute may obstruct the operation.

It is an object of the present invention to provide an automatic analyzer and a part feeding device in which a compact system configuration can be used to feed unused parts to be contacted with samples and to recover part racks from which the parts have been consumed.

It is another object of the present invention to provide an automatic analyzer and a part feeding device which can feed a large number of part racks holding unused parts, while keeping them stacked together, and which can simply separate and take out only the uppermost part rack from the other stacked part racks.

The present invention is applied to an automatic analyzer that analyzes samples using disposable parts used in contact with the samples and changed to new ones for each sample.

A concept based on the present invention is characterized by comprising a lift that raises a plurality of part racks holding unused disposable parts, from the bottom of the analyzer to a rack separation station, located above, while keeping the part racks stacked together, a rack separator that hinders the uppermost one of the plurality of stacked part racks from being lowered when the lift lowers, while allowing the other part racks to lower, so that the uppermost rack is separated from the other part racks so as to remain in the rack separation station, and a rack recovering part that operates after the parts on the separated part rack have been consumed, to move this empty part rack downward for recovery.

In a desirable embodiment to which the present invention has been applied, each fed part rack holds a plurality of disposable nozzle tips and disposable reaction containers. Further, the rack separator has a pair of hindering members that hinder the uppermost part rack from lowering. The pair of hindering members operate so that their interval increases when the uppermost part rack is raised to the rack separation station and decreases after the uppermost part rack has passed by the position of the pair of hindering members and before the second part rack from the top passes by the position of the pair of hindering members, thereby separating the uppermost part rack from the second part rack.

In the desirable embodiment of the present invention, a part rack taken out from the rack separation station and then moved to a part take-out station is pressed by a rack positioning device at a plurality of points thereof so as to rest at a predetermined position. Then, a part take-out device takes out disposable parts from the thus positioned part rack one by one. In this case, the part rack has positioning recesses formed at a pair of opposite upper edges thereof, and the rack positioning device comprises members that abut against the positioning recesses.

A part feeding device based on the present invention comprises a supply lifter having a lift that can move a plurality of part racks while keeping them stacked together, the part racks each holding a plurality of disposable parts used to handle samples, the lift being raised to a rack separation station when the rack separation station can receive new part racks, a rack separator that takes out the uppermost one of the stacked part racks from the rack separation station so as to separate the uppermost part rack from the other part racks, a rack feeding device that moves the separated part rack in a horizontal direction from the rack separation station to a part take-out station, and a recovery lifter having a lift that receives the part rack from which the parts have been consumed while the part rack is on the part take-out station, at a position higher than the lowest position after part consumption.

BEST MODE FOR CARRYING OUT THE INVENTION

An embodiment to which the present invention has been applied will be described with reference to the drawings. An automatic analyzer as a preferred embodiment analyzes samples using disposable parts used in contact with the samples and changed for each sample. In this example, the disposable parts include nozzle tips and reaction containers, but it is not always necessary to use both types of parts. One of these types may solely be used, or disposal parts other than the nozzle tips and reaction containers may be used. In either way, the disposable parts are two-dimensionally held on part racks, and the part racks are set on a lift so as to be stacked together and supplied.

Figure 1:
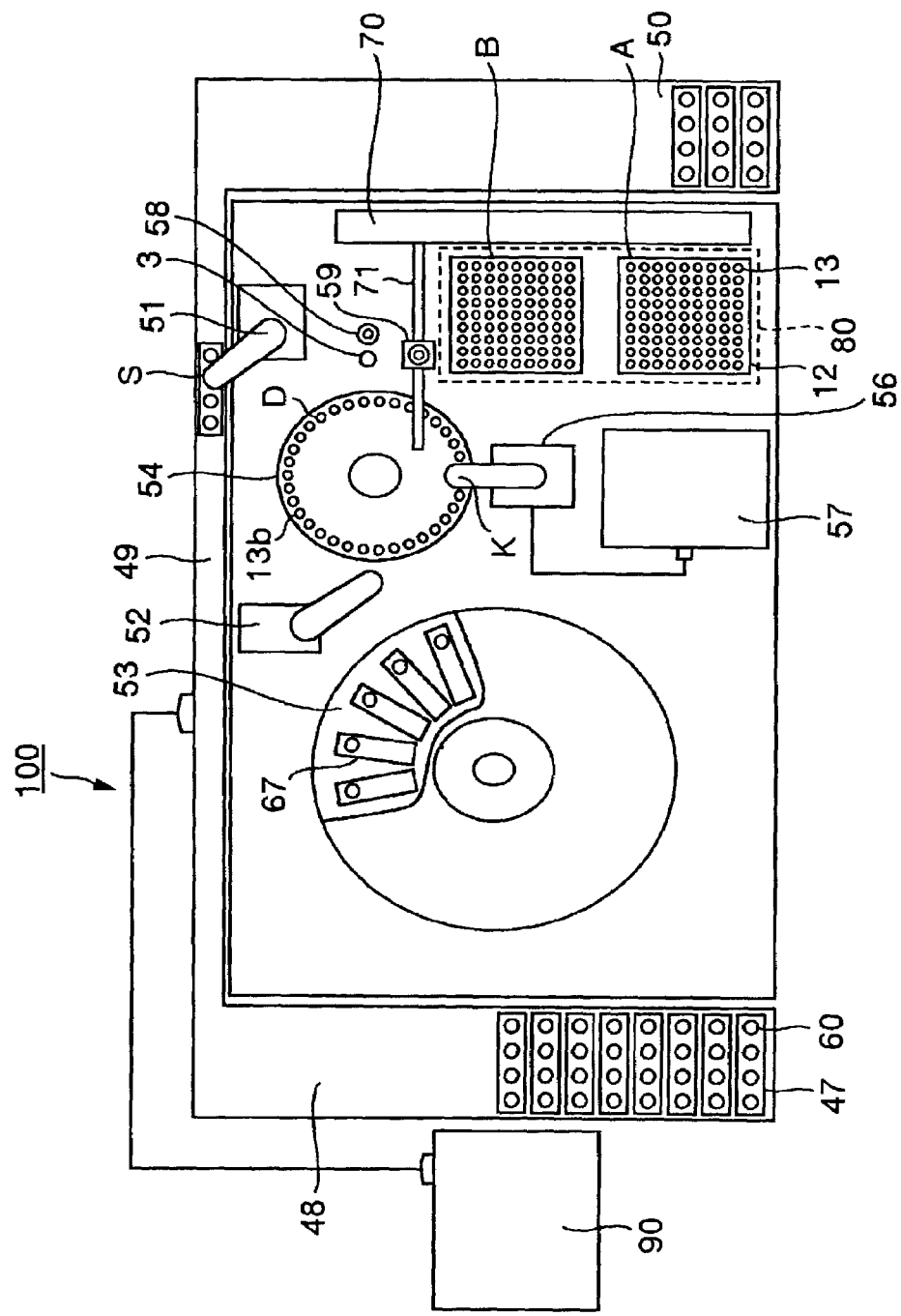
FIG. 1 is a schematic plan view showing an entire configuration of an automatic analyzer as an embodiment to which the present invention has been applied.

A part feeding device 80 incorporated in an automatic analyzer 100 in FIG. 1 comprises a rack separation station A and a part take-out station B in an area which is open to the exterior and which is at the highest position. As described later, a feeding lift 83 for unused part racks is arranged below the part take-out station A, and a recovering lift 84 for used part racks is arranged below the part take-out station B. The automatic analyzer 100 analyzes and measures living samples such as blood plasma, serum, or urine.

Each constituting mechanism part of the automatic analyzer 100 in FIG. 1 has their operations controlled by a controller 90. The automatic analyzer 100 comprises a subject carrier conveying system having a subject loader 48, a subject conveyance line 49, and a subject stocker 50, an analysis and measurement system having a reaction disk 54, a reagent disk 53, and a measuring part 57, and a disposable part handling system having the part feeding device 80 and a part transporting device 70. Samples to be analyzed and measured are accommodated in a sample container 60, and a box-shaped subject carrier 47 has a plurality of sample containers 60 loaded therein. Preferably, one subject carrier 47 has five or ten sample containers held therein. Information on the samples in the sample container 60 and information on requested analysis items are input beforehand through an input part of the controller. The analysis conditions for each analysis item are stored in the controller 90.

Each sample container 60 has a subject identification information medium such as a bar code provided on an outer wall thereof, and each subject carrier 47 has a carrier identification information medium such as a bar code provided thereon. The subject carrier 47 with subject containers loaded therein is set in the subject loader 48 by an operator. The subject loader 48 feeds the subject carrier 47 to the subject conveyance line step by step. Upon receiving the subject carrier 47, the subject conveyance line 49 coveys the subject carrier to a sample extraction position S. Before the subject carrier is transported to the sample extraction position, carrier identification information on each subject carrier and/or subject identification information on each sample container is read by an identification information reader (not shown) such as a bar code reader, and is then transmitted to the controller 90. On the basis of the read information, the controller 90 controls the operation of a subject sampling mechanism 51, the reagent disk 53, a reagent dispensing mechanism 52, the reaction disk 54, the measuring part 57, and others. The subject carrier 47, subjected to a sample extracting process at the sample extraction position S, is transported through the subject conveyance line 49 to the subject stocker 50, where it is stored.

In the part handling system, the part feeding device 80 provides nozzle tips and reaction containers both used to avoid carryover or contamination between the samples. These disposable parts are moved through the part feeding device 80 while being two-dimensionally held on a part rack 12. The part transportation device 70 sets one of the disposable reaction containers as parts 13 arranged on the part rack 12 located on the part take-out station B, on the reaction disk 54, and then sets one of the disposable nozzle tips as parts arranged on the same part rack, on a tip installation position 58. A tip coupling nozzle of the subject sampling mechanism 51 couples to the nozzle tip at the tip installation position 58, and subsequently the subject sampling mechanism 51 performs a sample extraction operation.

The part transportation device 70 comprises a movable holding part 59 which can hold the nozzle tip or reaction container and which can slide along a guide bar 71. Further, the guide bar 71 can move along a rail extending in the direction orthogonal thereto. Thus, the holding part 59 can freely move in both X and Y directions two-dimensionally and in a vertical direction at a predetermined position. The subject sampling mechanism 51 comprises a nozzle to which the nozzle tip is joined and a pump that is in communication with the nozzle. The subject sampling mechanism 51 functions as a pipetter.

When the subject carrier 47 is transported to the sample extraction position S, the nozzle of the subject sampling mechanism 51, to which the nozzle tip has already been connected, pivots to the sample extraction position, and a tip of the nozzle tip is inserted into the sample in the sample container 60 to suck a predetermined amount of sample in the nozzle tip. Then, the nozzle is raised and caused to pivot to the reaction disk 54, and then ejects the sample contained in the nozzle tip, into a disposable reaction container 13b located at a sample reception position D on the reaction disk 54. The nozzle, which has finished pipetting the sample, is caused to pivot to a part waste position 3, where the used nozzle tip is removed from the nozzle. Then, the nozzle tip is thrown away into a waste part recovery box through a hole formed at the part waste position 3, the waste part recovery box being arranged below the hole.

On the other hand, the reaction container 13b, which has received the sample at the sample reception position D, is rotationally moved to a reagent reception position R by the reaction disk 54. At this position, the reaction container 13b receives a reagent corresponding to an analysis item to start reaction. The reagent disk 53 holds a plurality of reagent bottles 67 accommodating reagents corresponding to various types of analysis items, and sets a reagent bottle corresponding to the analysis item on the reaction disk 54, at a reagent suction position. The reagent pipetting mechanism 52 sucks a predetermined amount of reagent in the reagent bottle 67 using a pipet nozzle, and then ejects the reagent into the reaction container 13b on the reaction disk 54.

The mixture of the sample and reagent is allowed to react on the reaction disk 54 for a predetermined time, and the reaction container 13b, in which a reaction product has been formed, is moved to a reacted liquid suction position K by a rotating operation of the reaction disk 54. A reacted liquid sucker 56 has a suction nozzle connected to a flow cell of the measuring part 57 to suck the reacted liquid from the reaction container located at the reacted liquid suction position K to thereby introduce it into the flow cell. The measuring part 57 carries out measurements on the introduced reacted liquid using, for example, a photometer. The used reaction container 13b, into which the reacted liquid has been sucked, is moved to a predetermined position by rotation of the reaction disk 54. At this position, the reaction container 13b is held by the holding part 59 of the part transportation device 70, and then transported to the part waste position 3, where it is thrown away into the waste part recovery box.

Now, the detailed configuration of the part feeding device 80 will be described with reference to FIGS. 2 to 7. The part feeding device 80 has the rack separation station A, the part take-out station B, and a rack waste station installed in an open area located at the upper end thereof. The part take-out station B may be aligned with the position of the rack separation station A or rack waste station, or may be arranged between the rack separation station A and the rack waste station. In the automatic analyzer in FIG. 1, the part take-put station B is aligned with the position of the rack waste station. In this desirable embodiment, the part take-out station B does not overlap the rack separation station, so that while the part transportation device 70 is continuing taking out parts from the current part rack on the part take-out station B, a new part rack 12 with unused part mounted thereon can be moved to the rack separation station A. Consequently, once all the parts on the current part rack have been consumed, the new part rack can be immediately fed to the rack take-out station B, thereby enabling an efficient part take-out operation.

Figure 3:
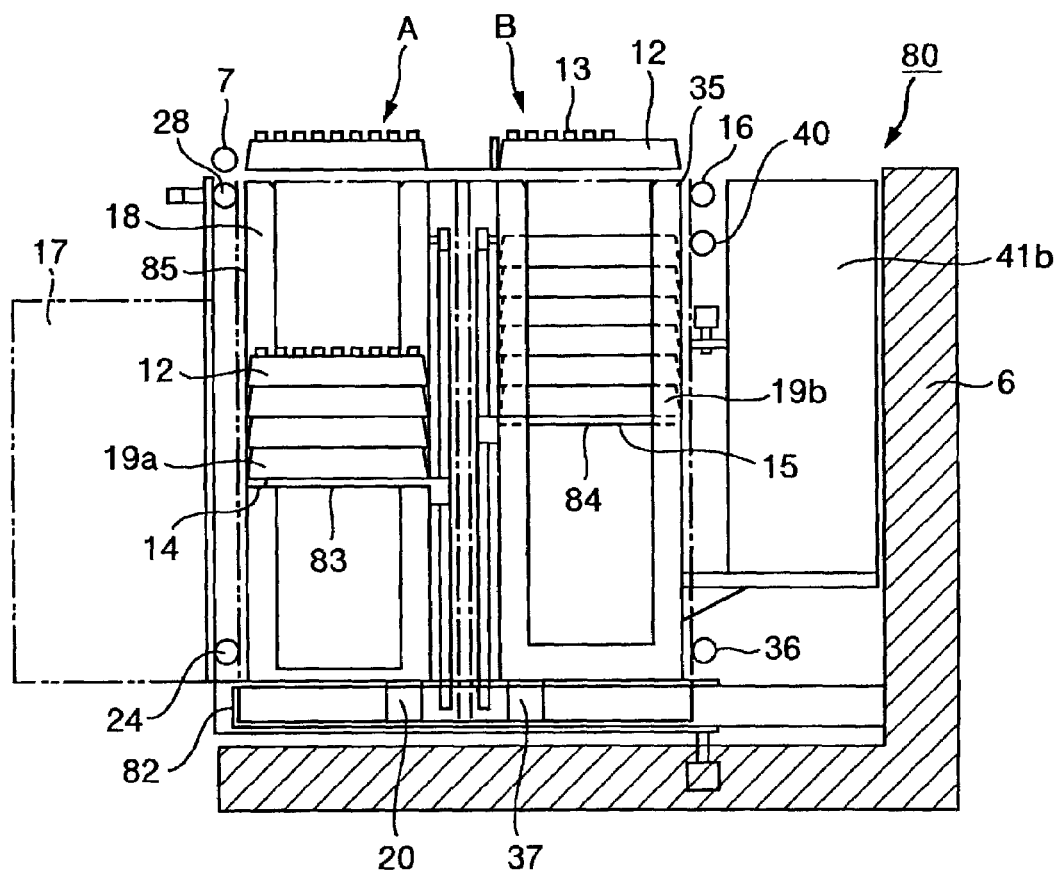
FIG. 3 is a side view of the interior of a rack lift chamber of the part feeding device in FIG. 2.
Figure 4:
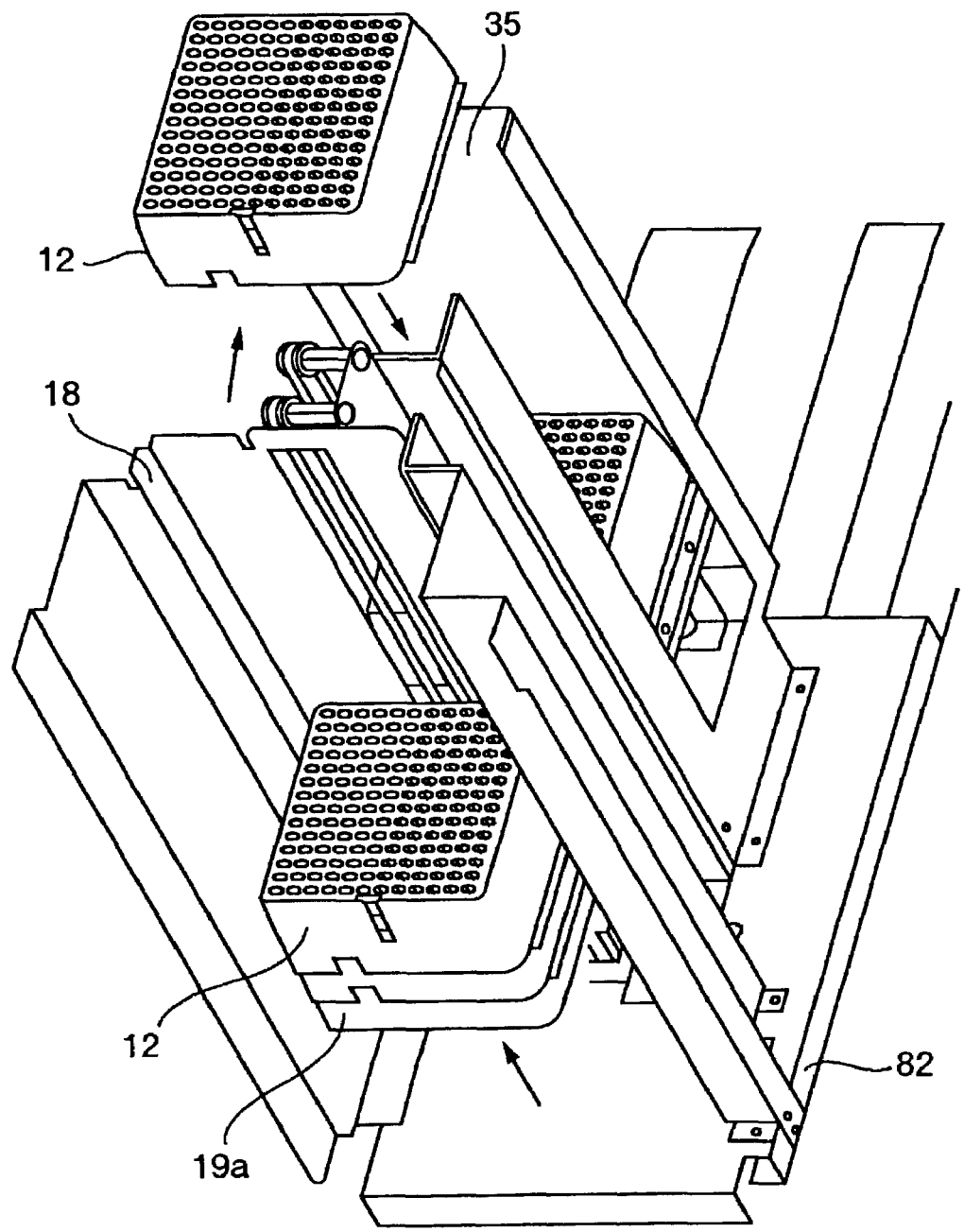
FIG. 4 is a partial perspective view of the vicinity of the rack lift chamber in FIG. 2.
Figure 5:
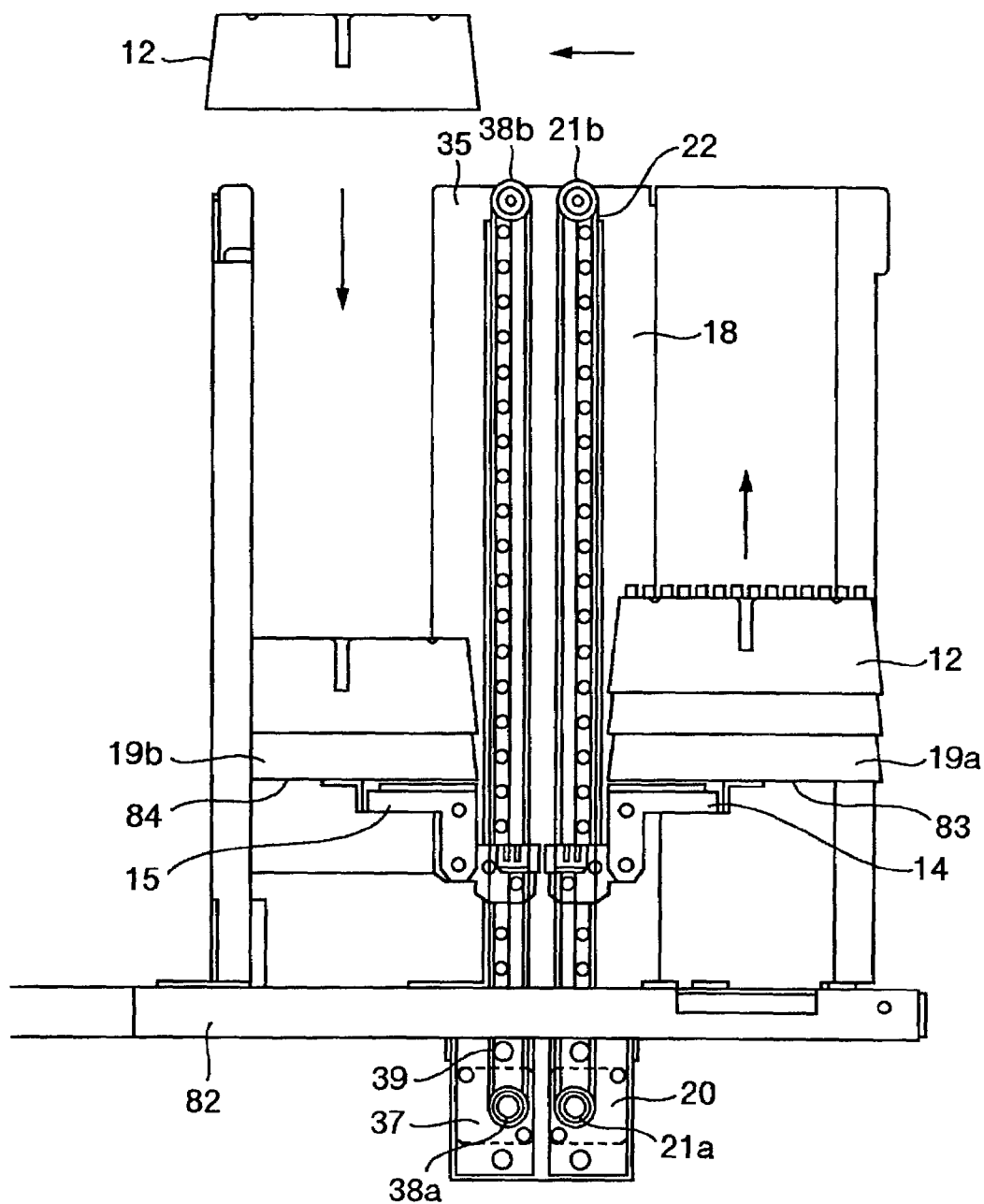
FIG. 5 is a side view showing a supply and recovery rack lifters as viewed from a rear side of FIG. 3.

As shown in the detailed configuration in FIGS. 3, 4, and 5, a supply lifter 14 is arranged below the rack separation station A, and a recovery lifter 15 is arranged below the part take-out station B. The lifts 14 and 15 are housed in a rack lift chamber 85 of the part feeding device 80. Further, these lifts are mounted on a movable table 82. The rack lift chamber 85 has a door 17 installed at a front surface thereof and for which an electromagnetic lock is operated by the controller 90. Only when both the lift 83 of the supply lifter 14 and a lift 84 of the recovery lifter 15 are at their lowest positions (bottom dead centers), the electromagnetic lock can be cleared to open the door 17. Safety measures are provided such that while the lifts 14 and 15 are in operation or immediately before they start operations, the controller 90 automatically locks the door 17 to prevent the operator from loading a part rack in the rack lift chamber 85 or taking out an empty part rack from the rack lift chamber 85 while the lifts are in operation.

When the door 17 is opened, the lifts 14 and 15 can be pulled out from the rack lift chamber 85 toward its front surface side together with the movable table 82. The operator can then set a new part rack 12 on the feeding lift 83 and remove a used part rack from the recovering lift 84. The rack lift chamber 85 has two removable waste part recovery boxes 41a and 41b (FIG. 2) arranged inside the rack lift chamber 85 along a rear wall 6 so as to lie below the part waste position 3 in FIG. 1. When the pulled-out movable table 82 is pushed to a predetermined position, the lifts 14 and 15 are settled at their original positions where the lifts 83 and 84 can be raised and lowered.

Figure 6:
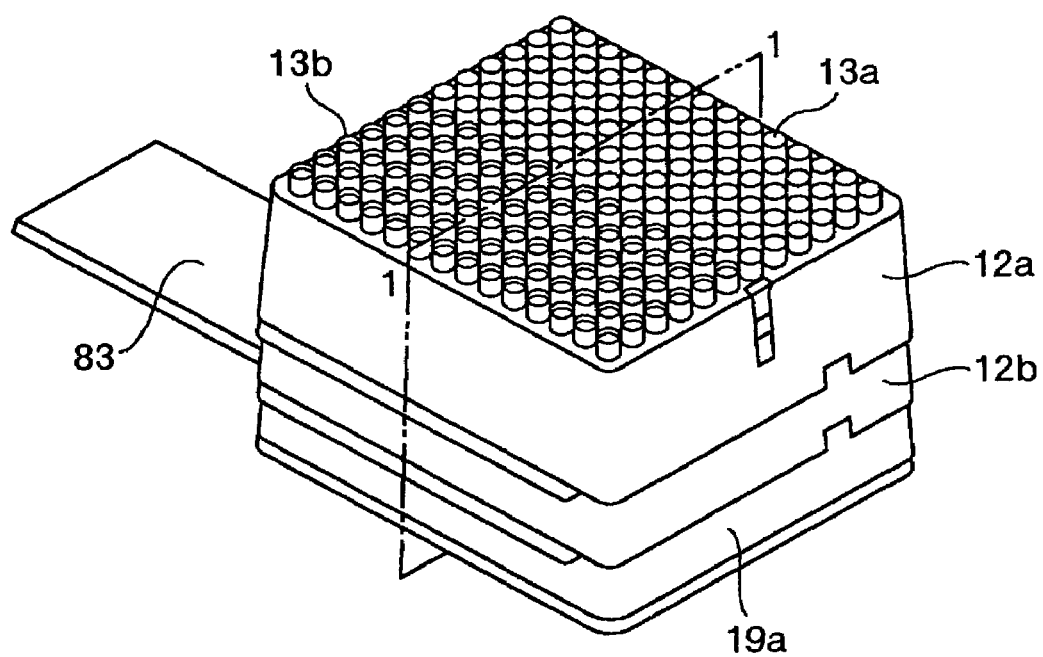
FIG. 6 is a perspective view showing that a plurality of part racks are placed on a receiving member of the lifter.
Figure 7:
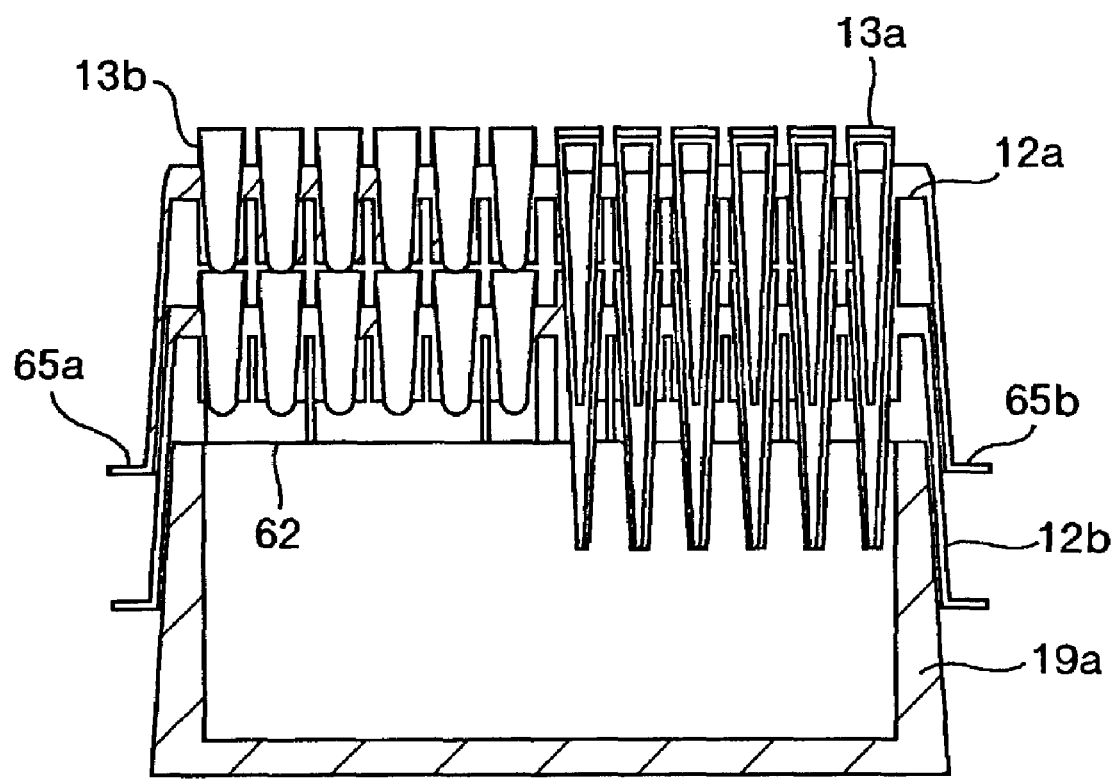
FIG. 7 is a sectional view taken along a line 1-1 in FIG. 6.

As is apparent particularly from FIGS. 6 and 7, the part rack 12 is shaped like a box having a four trapezoidal sides, and is molded of plastics. Four side walls each have a lower edge larger than an upper edge and are thus inclined to widen downward so that part racks can be stacked together. A cavity is formed inside the side walls, and no bottom wall is installed at the bottom of the part rack. The top surface of the part rack 12 is generally rectangular and has holes two-dimensionally arranged thereon and in which a large number of disposable parts can be installed. In the example in FIG. 6, 14×12 holes are formed and each have a part inserted thereinto. A plurality of disposable nozzle tips 13a and a plurality of disposable reaction containers 13b can be installed on a single part rack 12. In the example in FIG. 6, a number of nozzle tips and the same number of reaction containers are held thereon.

The part rack 12 has protruding parts 65a and 65b formed at the lower ends of at least two opposite side walls and each having a predetermined width and length. The pair of protruding parts 65a and 65b abut against a lowering hindering member of a rack separator, described later, to facilitate separation of part racks. A thin rib 62 is formed vertically downward from a top face in the internal space of each part rack 12 enclosed by the side walls, so as not to obstruct insertion of parts. The rib 62 is formed like a cross that crosses at the center of a single part rack. The depthwise distance of the rib 62 is half or less of the height of the part rack. The presence of the rib 62 serves to maintain a fixed interval between the top surfaces of part racks even when they are stacked together, thereby forming a small gap between the side walls of stacked part racks. Consequently, the upper part rack can be separated from the lower part rack.

As is apparent from FIGS. 3, 5, 6, and 7, the supply lifter 14 and the recovery lifter 15 have similar structures. The lift 83 of the supply lifter 14 has a receiving member 19a mounted thereon and having an outward form similar to that of the part rack 12. The lift 84 of the recovery lifter 15 has a receiving member 19b mounted thereon and having the same shape. These receiving members are each shaped like a box having a lower end larger than an upper end so that when the part rack 12 is placed on the receiving member from above so as to cover it, the rack 12 fits the receiving member. These receiving members can each move into the part rack. Simply by placing the part rack 12 holding unused parts, on the receiving member 19a, this part rack can be precisely positioned so as not to incline even when other part racks are staked thereon. Further, the receiving member 19b of the recovering lift 84 can maintain the positions of part racks so that the part racks will not significantly deviate from their regular positions (where the top surfaces of the part racks are level) upon receiving an empty part rack.

The rack lift chamber 85 comprises a rack feeding part having the supply lifter 14, and a rack recovering part having the recovery lifter 15. A guide wall 18 of the rack feeding part forms a generally vertical lift path to maintain the longitudinal and transverse directions of a plurality of part racks 12 holding unused parts so as to prevent the racks from collapsing when the lift 83 is raised and lowered with the part racks stacked together. A guide wall 35 of the rack recovering part forms a generally vertical lift path to maintain the longitudinal and transverse directions of a plurality of stacked part racks so as to prevent the racks from collapsing when the lift 84 is raised and lowered after receiving a plurality of empty part racks while keeping them stacked together, from which the parts have been consumed. Consequently, the feeding and recovering lifts 83 and 84 are raised and lowered through a limited space via the guide walls, which are arranged to fit the size of the part rack 12.

The movable table 82 has the supply lifter 14 and the recovery lifter 15 mounted thereon, and the lift 83 of the supply lifter 14 is driven by a pulse motor 20. A timing belt 22 is extended in the vertical direction between a lower pulley 21a and an upper pulley 21b. Rotational force from the pulse motor 20 is transmitted via the pulleys and timing belt to the lift 83, which is attached to the timing belt 22, so that the lift 83 is moved in the vertical direction. The lift 84 of the recovery lifter 15 is driven by a pulse motor 37. A timing belt 39 is extended in the vertical direction between a lower pulley 38a and an upper pulley 38b. Rotational force from the pulse motor is transmitted to the lift 84, which is attached to the timing belt 39, so that the lift 84 is moved in the vertical direction. The rack feeding part has a position sensor 24 arranged at the bottom thereof for detecting the lowest position (bottom dead center) of the lift 83. Further, the rack recovering part has a position sensor 36 arranged at the bottom thereof for detecting the lowest position (bottom dead center) of the lift 84.

Near the rack separation station A, located at the top of the rack feeding part, are arranged an uppermost position sensor 7 for detecting the uppermost one 12a of the stacked part racks when it is separated from the other part racks and a second position sensor 28 for detecting the second part rack 12b during a rack separating operation. At a height close to the part take-out station B, located at the top of the rack recovering part, are arranged a fall detecting sensor 16 for detecting the part rack 12 falling from the part take-out station B and an uppermost position sensor 40 for adjusting the height of the uppermost one of a plurality of stacked part racks when the recovering lift 84 is to receive an empty rack.

The part feeding device 80 comprises a rack separator 8 that separates and holds only the uppermost one of a plurality of stacked part racks in the state separated from other part racks so as to leave it in the rack separation station, the plurality of part racks having been raised to the rack separation station from the lowest position by the lift 83 of the supply lifter 14, a set position; a rack transferring device 95 that moves the uppermost part rack separated from the other part racks by lowering the lift 83 in the direction of the part take-out station B from the rack separation station; a rack positioning device 75 that positions the part rack delivered to the part take-out station B by pressing the part rack at a plurality of points thereof to settle it at a predetermined position; a floor-part opening and closing device 11 that opens the floor part (an openable and closable member) on which the part rack is placed at the part take-out station B when the lift 84 of the recovery lifter receives the part rack from the part take-out station, the floor-part opening and closing device subsequently closing the floor part; and other components.

The operator pulls out the movable table 82 to the front surface of the part feeding device, places a plurality of part racks holding unused disposable parts (in this example, nozzle tips and reaction containers) so as to stack together, on the feeding lift 83, and then closes the door 17. If the rack separation table A is ready to receive a new part rack, the lift 83 is raised to the rack separation table A. The uppermost part rack 12a of the stacked part racks is sensed by the uppermost position sensor 7 when it reaches the rack separation station, and on the basis of this detection, the rack separation device 8 holds the uppermost part rack 12a so as to hinder it from falling from the rack separation station. When the lift 83 lowers from the rack separation station, the rack separator 8 hinders the uppermost part rack 12a from falling, while allowing the other part racks including the part rack 12b, which has been located at the second position in the initial stack state, thereby leaving the uppermost part rack 12a on the rack separation station. After the separating operation, the lift 83 is lowered to the lowest position.

During the descent of the lift 83, the part rack 12b, which has been located at the second position from the top in the initial stack state (the uppermost position during the descent), is sensed by the second position sensor 28. On the basis of sensed information from the uppermost position sensor 7 and second position sensor 28, the control part 90 determines whether or not the uppermost part rack 12a has been properly separated in order to determine whether to continue the operation of the part feeding device 80 or interrupting the operation and alarming the operator. The part transporting device 70 takes out disposable parts from the part rack on the part take-out station B one by one. During this time, the floor-part opening and closing device 11 closes the opening and closing member so that the part rack is fixed to the part take-out station B. Once all the disposable parts on the part rack on the part take-out station have been consumed, the floor-part opening and closing device 11 opens the opening and closing member to drop the part rack downward so that this used empty part rack can be received on the recovering lift 84. Thus, this part rack is recovered so that a plurality of empty part racks are stacked together on the lift 84. The lift 84 is raised to a position closer to the part take-out station than to the lowest position before receiving the part rack. Accordingly, the distance that the part rack must fall before reaching the lift 84 is reduced to ensure recovery, and possible noise produced during the fall is reduced. After receiving the part rack, the lift 84 is lowered to the lowest position.

According to this embodiment, unused disposable parts contacted with samples when used in the automatic analyzer can be fed upward while being held on a part rack, and an empty rack from which the parts have been consumed can be recovered by moving it downward, thereby achieving a generally compact configuration. Further, a plurality of part racks holding unused parts are fed to the rack separation station while being stacked together on the feeding lift, and the uppermost one of the stacked part racks can be solely and easily separated from the other part racks and taken out. A plurality of used empty part racks can be recovered so as to be stacked together on the recovering lift, allowing the size of the rack recovering part to be reduced. Furthermore, the supply lifter and the recovery lifter can be arranged adjacent to each other so as to rise and lower parallel with each other, thereby allowing the part feeding device to be constructed with a reduced floor area.

Figure 8:
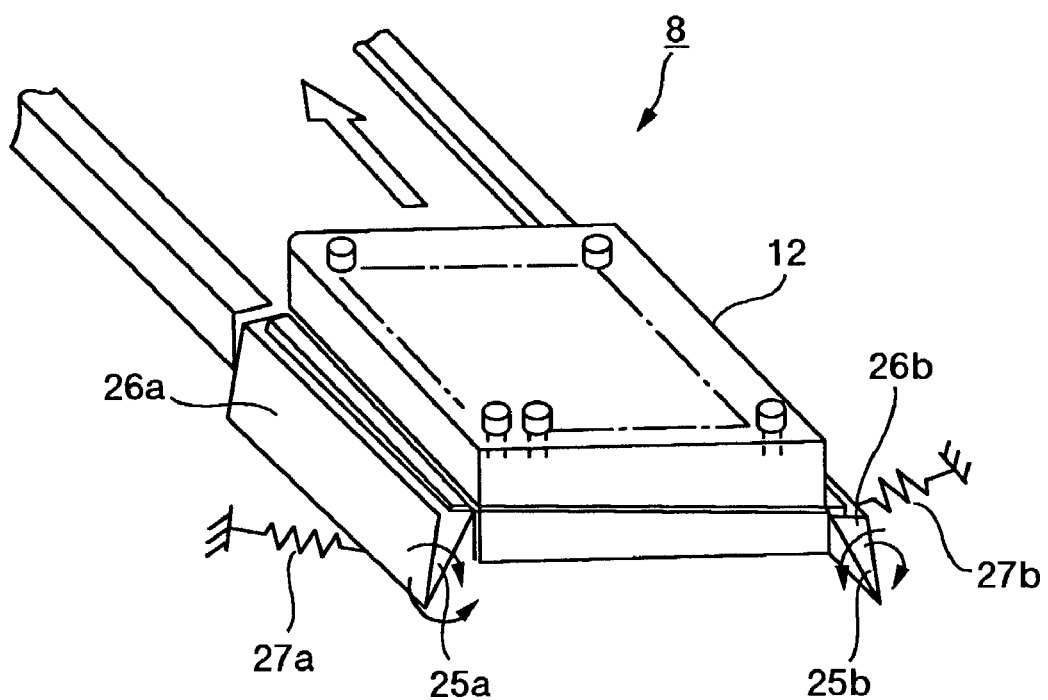
FIG. 8 is a perspective view illustrating functions of a rack separating mechanism of the part feeding device.
Figure 9:
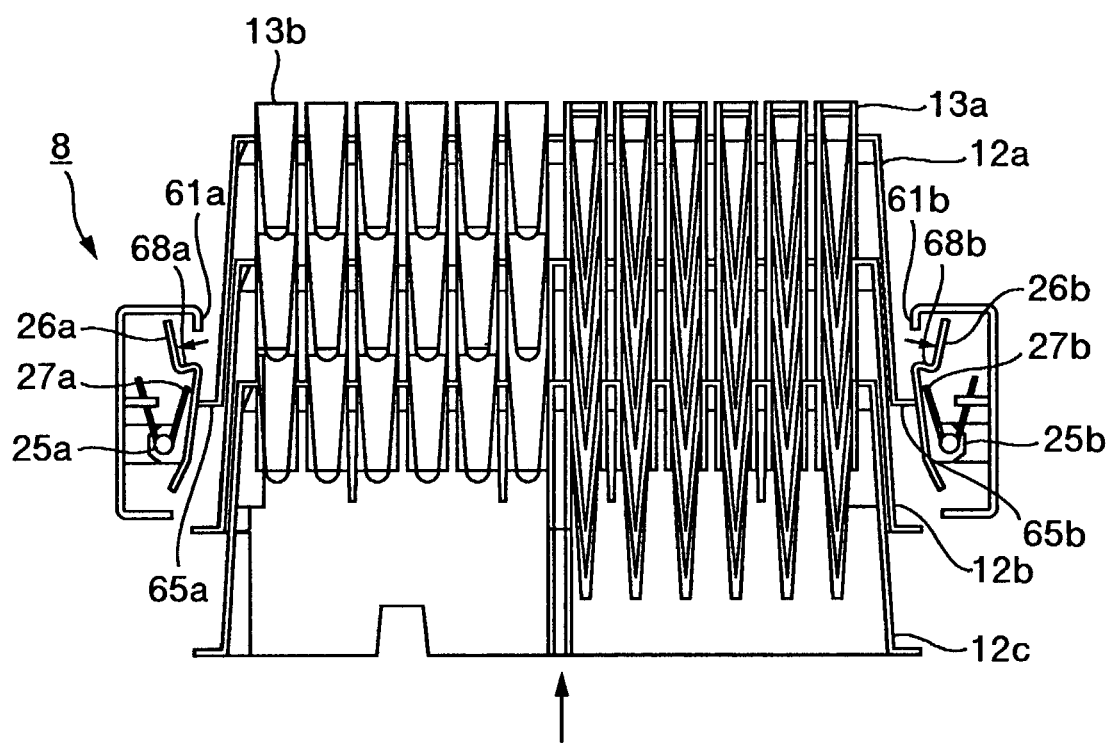
FIG. 9 is a sectional view illustrating an operation of the rack separating mechanism performed when the supply lifter is raised.
Figure 10:
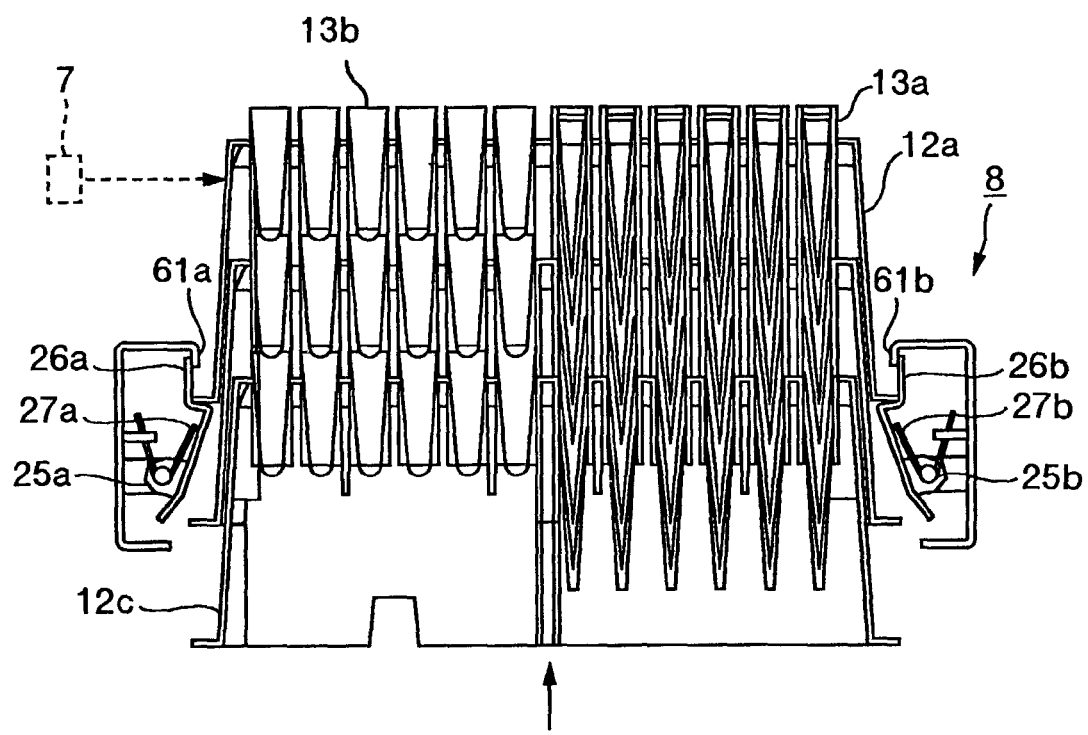
FIG. 10 is a sectional view showing conditions of the rack separating mechanism observed when the supply lifter is at the highest position.
Figure 11:
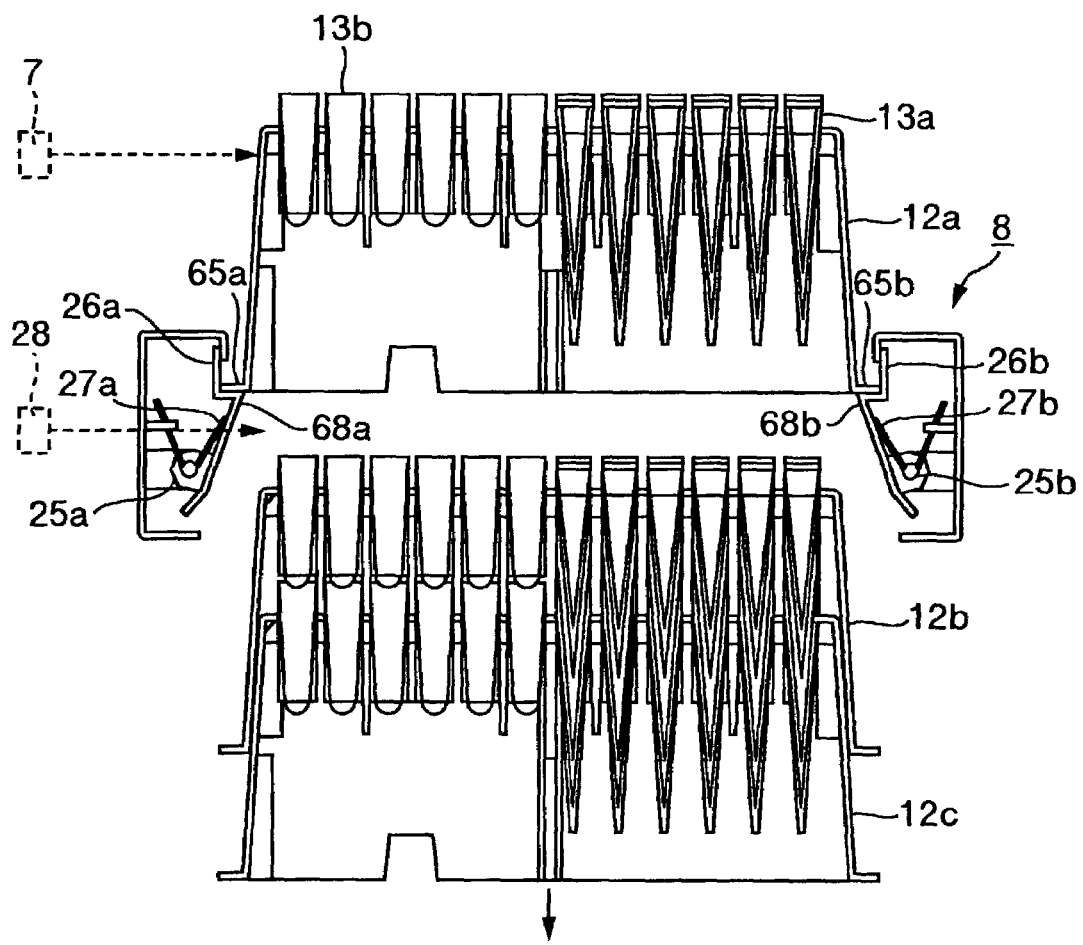
FIG. 11 is a sectional view showing conditions of the rack separating mechanism observed when the supply lifter lowers while leaving the uppermost part rack.

Now, the rack separator for separating the uppermost part rack from the supply lifter will be described with reference to FIGS. 8, 9, and 10.

The rack separating mechanism 8 has a pair of hook bars 26a and 26b separated so as to leave a space therebetween the size of which matches the width of the part rack. The transversally long hook bars 26a and 26b are attached to rotating shafts 25a and 25b in such a manner that their transversally long directions are parallel. The transversally long hook bars 26a and 26b are formed of relatively thin metal (for example, stainless steel) and are thus somewhat elastic. The hook bars 26a and 26b have shell parts 68a and 68b, respectively, formed in the vertical middle thereof and on which the protruding parts 65a and 65b of the part rack 12 can be laid. The hook bars 26a and 26b have their sides pressed by torsion springs 27a and 27b, respectively, attached to the rotating shafts 25a and 25b, respectively. The springs 27a and 27b may pull the lower ends of the hook bars 26a and 26b, respectively, as shown in FIG. 8. The essential point is that the shelf parts 68a and 68b of the hook bars normally undergo such rotational force that the shelf parts are closed in the direction (inward) in which they approach each other.

The hook bars 26a and 26b have their upper ends abutted against stoppers 61a and 61b, respectively, which restricts rotation of the hook bars so as to prevent them from being closed beyond their predetermined positions. While the hook bars 26a and 26b are abutting against the stoppers 61a and 61b, respectively (normal state), the distance between the pair of shelf parts 68a and 68b is smaller than that between the tips of the pair of protruding parts 65a and 65b of the part rack 12 and larger than the width of the part rack 12 excluding the protruding parts 65a and 65b.

The rack separation station A can receive a part rack when it has no part racks. In this case, the upper ends of the hook bars 26a and 26b abut against the stoppers 61a and 61b, respectively. A plurality of part racks 12 holding unused disposable parts 13a and 13b are raised by the feeding lift 83 while being stacked together. When the uppermost stacked part rack 12a is raised and passes between the pair of hook bars 26a and 26b, the protruding parts 65a and 65b, abutted against the sides of the hook bars 26a and 26b, respectively, push open the hook bars 26a and 26b, respectively, as the part rack is raised. That is, the force applied by the supply lifter 14 to raise the part rack 12a pushes open the hook bars 26a and 26b outward against the force of the springs 27a and 27b, which operate to reduce the distance between the hook bars. This is shown in FIG. 9.

When the uppermost part rack 12a is further raised, the protruding parts 65a and 65b of the part rack 12a pass by the shelf parts 68a and 68b of the hook bars 26a and 26b, respectively, thereby narrowing the hook bars 26a and 26b due to the spring force. Consequently, the interval between the shelf parts 68a and 68b becomes smaller than the interval between the protruding parts 65a and 65b. This is shown in FIG. 10. At this timing, the uppermost position sensor 7 senses the uppermost part rack 12a and transmits a sensor signal to the controller 90. On the basis of this sensor signal, the controller 90 controls the supply lifter 14 to stop lifting. In this case, the protruding parts of the second part rack 12b from the top are kept in the state present before they come into contact with the hook bars 26a and 26b. Accordingly, the hook bars 26a and 26b remain closed.

Then, the feeding lift 83 starts a lowering operation. At this time, the shelf parts 68a and 68b of the hook bars 26a and 26b acts as a pair of hindering members for hindering the part rack 12a, located at the uppermost position during the ascent, from lowering. That is, the part racks 12b, 12c, located at the second and subsequent positions during the ascent, lower due to their weights in such a manner as to follow the lowering operation of the lift 83. However, the part rack 12a, located at the uppermost position during the ascent, is not lowered because the shelf parts 68a and 68b of the hook bard 26a and 26b are narrowed to keep the protruding parts 65a and 65b sitting on the shelf parts 68a and 68b. This allows the uppermost part rack to be separated from the other part racks.

Once the lift 83 starts lowering, the second position sensor 28, arranged in the vicinity of the hook bars 26a and 26b for monitoring a position slightly lower than the lower end of the uppermost part rack 12a, determines whether or not the part rack 12a, located at the uppermost position during the ascent, is present. If the rack separation has been normally executed, the second position sensor does not sense the part rack. However, if the uppermost part rack 12a has lowered with the other part racks rather than being held by the rack separating mechanism 8, the second position sensor senses its presence. On the basis of sensor signals from the uppermost position sensor 7 and the second position sensor 28, the controller 90 judges whether or not the uppermost part rack 12a has been normally separated from the other part racks.

Subsequently, the lift 83 lowers to the lowest position (bottom dead center). At this time, if the uppermost part rack 12a has been normally separated from the other part racks, the part feeding device 80 continues to perform subsequent operations. However, if the uppermost part rack 12a has not been normally separated from the other part racks, the controller 90 stops the part feeding device 80 from performing subsequent operations, and causes a buzzer 45 such as the one shown in FIG. 2 to produce a warning sound and/or causes a display 44 such as a CRT to provide alarm information, thereby warning the operator.

Further, the controller 90 receives a signal from the position sensor 24 for detecting the lowest position, counts the number of pulses transmitted to the pulse motor 20 in order to lower the lift 83 from the highest position to the lowest position, calculates the number of part racks 12 remaining on the feeding lift 83 on the basis of the number of pulses, and shows, on the display 44, the number of remaining part racks and the number of part racks that can be added to the lift 83. In this case, at the same time, the number of disposable parts remaining on the lift 83 may be calculated and shown on the display 44.

Furthermore, if the number of part racks remaining on the lift 83 is smaller than a threshold preset in the controller 90, the controller 90 uses the buzzer 45 and the display 44 to warn the operator to urge him or her to add unused part racks to the lift 83. If both the lifts 83 and 84 are at the lowest positions, even when the part take-out station B is taking out parts, new part racks can be added to the feeding lift 83, while used part racks can be removed from the recovering lift 84.

Figure 2:
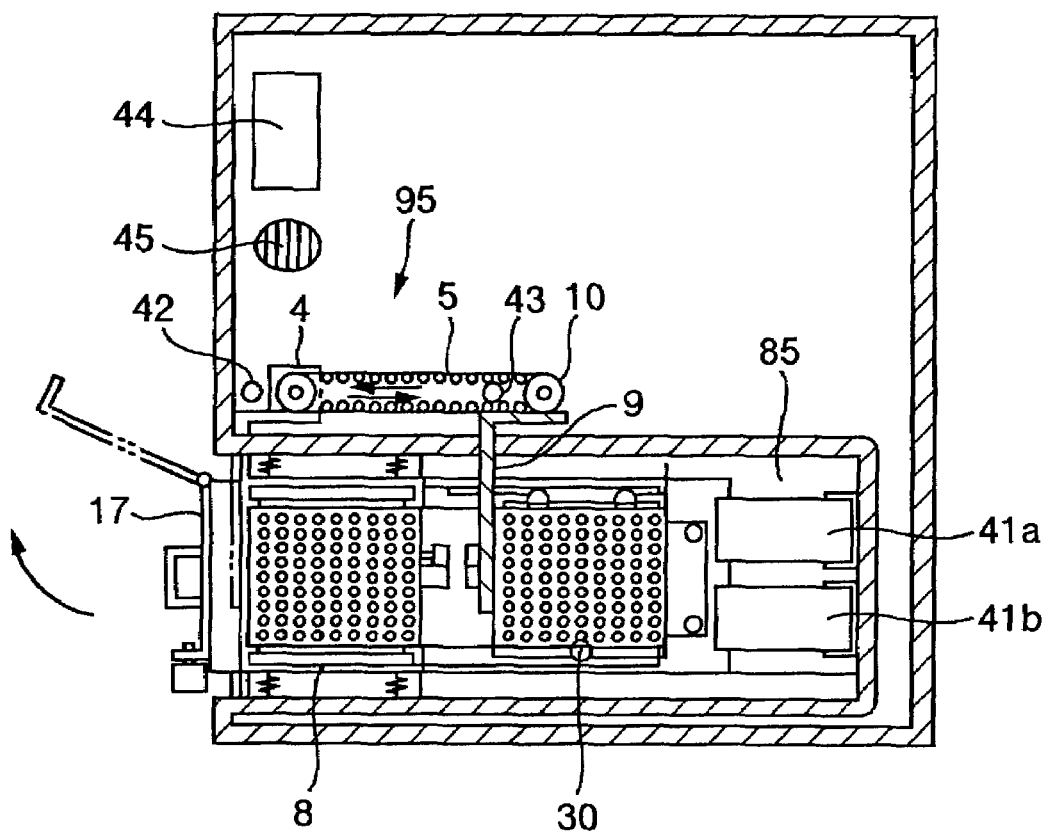
FIG. 2 is a schematic plan view illustrating the vicinity of a part feeding device of the automatic analyzer in FIG. 1.

The part rack 12*a*, separated from the other part racks 12*b* and 12*c* on the rack separation station A, is moved from the rack separation station A to the rack take-out station B by the rack feeding mechanism 95, shown in FIG. 2. The configuration of the rack feeding mechanism 95 will be described with reference to FIGS. 2 and 12.

The rack feeding mechanism 95 comprises the timing belt 5 installed so as to be rotationally moved between the rotating shaft of the pulse motor 4 and the pulley 10. The timing belt 5 has a shift lever 9 attached thereto. A driving operation performed by the pulse motor 4 causes the shift lever 9 to reciprocate between a standby position (see FIG. 12) located at the leading position of the rack separation station A and a position at which it is pushed out to the part take-out station (see FIG. 2). The part rack separated from the other part racks on the rack separation station A is positioned on the part take-out station B by causing the shift lever 9 to push the rear side of this part rack. The shift lever 9, which has pushed out the part rack 12*a* in the horizontal direction, returns to the original standby position before the new part rack 12*b* is fed to the rack separation station A. At this position, the shift lever 9 stands by so that the next part rack can be fed.

Figure 12:
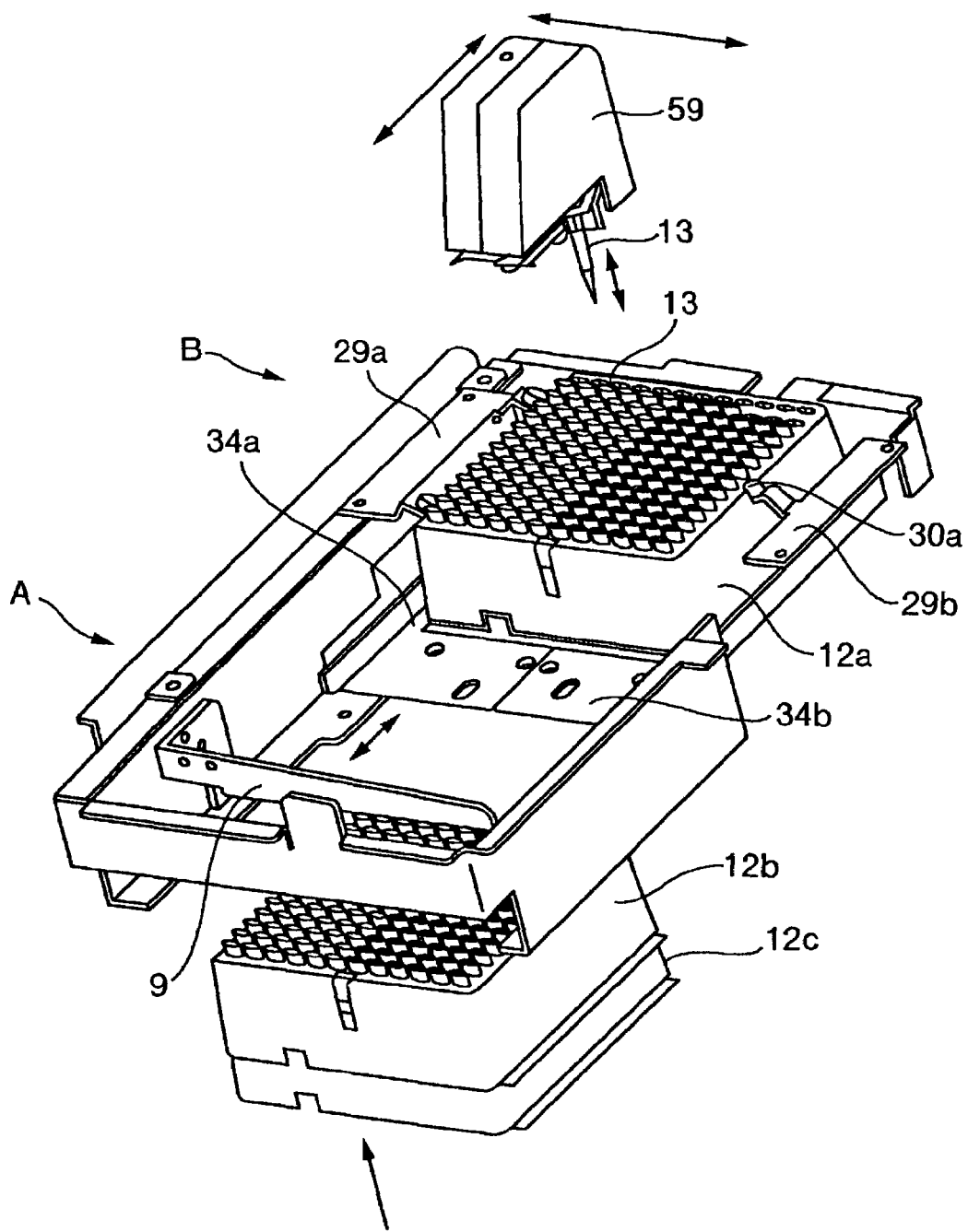
FIG. 12 is a partial perspective view illustrating that a part rack separated from the other part racks is moved to a part take-out station.
Figure 13:
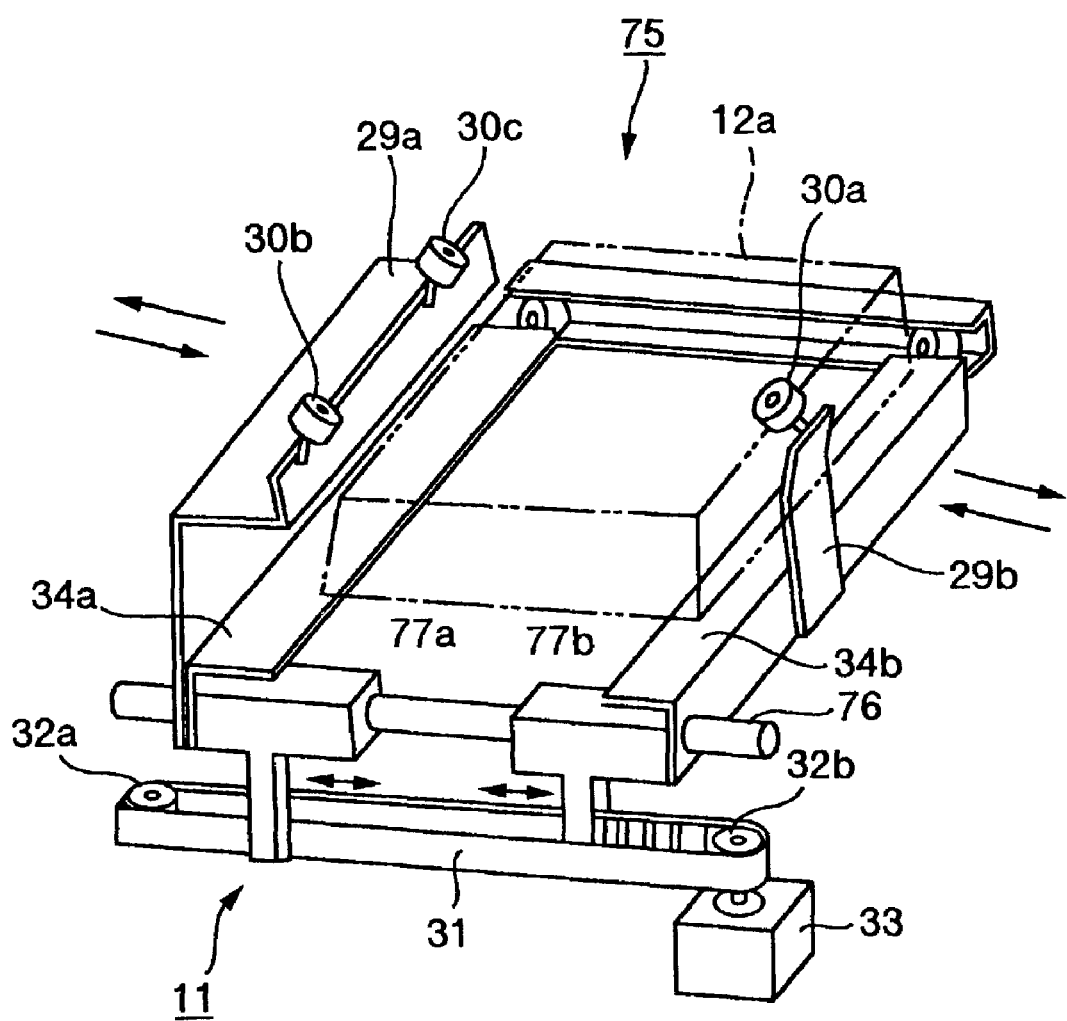
FIG. 13 is a partial perspective view illustrating an operation of a rack positioning mechanism and a floor part opening and closing mechanism both installed in a part feeding device.

A position sensor 43 senses that the shift lever 9 has reached the proper push-out position, and a position sensor 47 senses that the shift lever 9 has returned to the original standby position. As shown in FIGS. 12 and 13, the part rack 12*a*, which has reached the part take-out station B, is positioned by bearings 30*a*, 30*b*, and 30*c* as part rack pressing members of the rack positioning mechanism 75 so as to be properly fixed in all of the longitudinal, transversal, and vertical directions.

Figure 14:
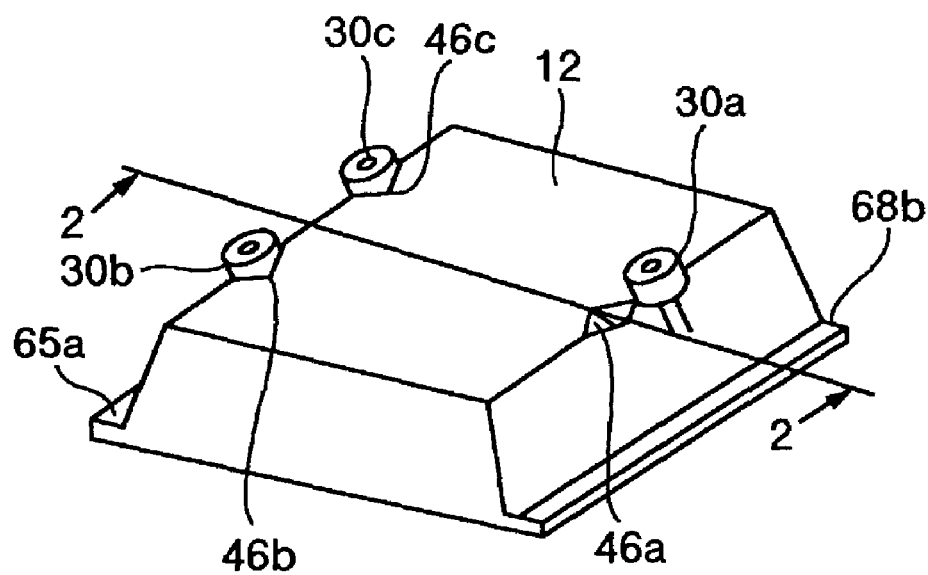
FIG. 14 is a schematic perspective view illustrating how a part rack is pressed by the rack positioning mechanism.

The rack positioning mechanism 75, arranged correspondingly to the part take-out station B, comprises two arms 29*a* and 29*b* formed of metal plates and arranged opposite each other. The larger arm 29*a* has the bearings 30*b* and 30*c* abutted against the part rack 12*a* and attached to the arm 29*a* at such an angle (for example, 45° relative to the horizontal) that pressure is exerted on the part rack 12*a* in both the vertical and horizontal directions. Additionally, the smaller arm 29*b* has the bearing 30*a* similarly attached thereto at such an angle (for example, 45°) that pressure is exerted on the part rack 12*a* in both the vertical and horizontal directions. These bearings are located correspondingly to a plurality of positioning recesses 46*a*, 46*b*, and 46*c* formed on parallel and opposite upper edges of the part rack 12 as shown in FIG. 14. When the part rack 12*a* is fixed in position, it is abutted so that each bearing is fitted in the corresponding recess.

The rack positioning mechanism 75 is operated in connection with the floor-part opening and closing mechanism 11 (FIG. 13). As shown in FIGS. 12 and 13, the floor part of the part take-out station B, on which part racks are placed, is composed of a pair of movable plates 34*a* and 34*b* that can be opened and closed in the horizontal direction. These movable plates constitute part of the floor-part opening and closing mechanism 11. The arm 29*a* of the rack positioning mechanism 75 is attached to the movable plate 34*a*, and the other arm 29*b* is attached to the movable plate 34*b*. The movable plate 34*a* is fixed to a slider 77*a*, and the other movable plate 34*b* is fixed to a slider 77*b*. The arms 29*a* and 29*b* in FIG. 13 have shapes slightly different from those shown in FIG. 12, but have the same functions as the arms in FIG. 12.

The sliders 77*a* and 77*b* can slide along a slide shaft 76. As the sliders slide, the pair of movable plates 34*a* and 34*b* change the interval therebetween while remaining parallel with each other, and function as a floor part when positioning a rack part or as a floor-part opening and closing member when recovering a part rack. The floor-part opening and closing mechanism 11 has a timing belt 31 extended between a pulley 32*b* attached to a rotating shaft of a pulse motor 33 and a pulley 32*a* located horizontally relative to the pulley 32*b*. The sliders 77*a* and 77*b* are set on the timing belt 31 so that as the timing belt 31, driven by the pulse motor, moves, the two sliders 77*a* and 77*b* approach or leave each other.

Figure 15:
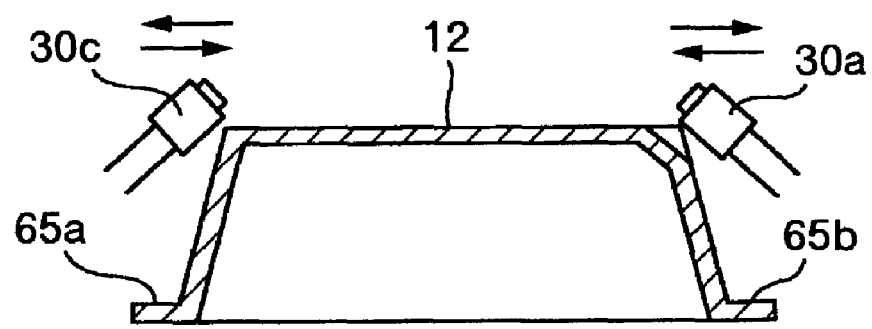
FIG. 15 is a sectional view taken along a line 2-2 in FIG. 14.

The floor-part opening and closing mechanism 11 opens and closes the movable plates 34*a* and 34*b* through three stages. The first stage corresponds to an open and close state of the movable plates 34*a* and 34*b* maintained when the part rack 12 is moved from the rack separation station A to the part take-out station B. At the first stage, as shown in FIG. 15, the arms 29*a* and 29*b* are half-opened so that the bearings 30*a* and 30*b* as rack pressing members will not contact with the transferred part rack 12. In this case, the interval between the two plates 34*a* and 34*b* is in an intermediate state in which the plates 34*a* and 34*b* can support the upper end (bottom) of the transferred part rack 12 so that the rack 12 will not fall. Before the part rack 12 is conveyed by the rack feeding mechanism 95, the movable plates 34*a* and 34*b* stand by while remaining open in the intermediate state, which corresponds to the first stage.

The second stage corresponds to an open and close state of the movable plates 34*a* and 34*b* maintained when the part rack 12 that has reached the part take-out station B is precisely positioned so as to be correctly taken out by the movable holding part 59 of the part transporting device 70. At the second stage, the interval between the pair of movable plates 34*a* and 34*b* is kept smallest among the three stages. The second stage is carried out after the first stage; the interval between the movable plates 34*a* and 34*b* is reduced so as to press the plurality of bearings 30*a*, 30*b*, and 30*c* against the part rack 12 on the movable plates 34*a* and 34*b*. Thus, the interval between the pair of arms 29*a* and 29*b* is reduced to abut and fix the three bearings against and to the three corresponding recesses 46*a*, 46*b*, and 46*c* in the part rack 12, sandwiched between the arms 29*a* and 29*b*, thereby precisely positioning the part rack on the part take-out station B in all of the longitudinal, transversal, and vertical directions.

The pressing members 30*a*, 30*b*, and 30*c* may each have a cylindrical shape as shown in the figure, or a spherical shape or another similar shape. When the part rack 12 is fixed in position, the pressing members (bearings) are fitted in the corresponding recesses 46*a*, 46*b*, and 46*c* to correct the horizontal position of the part rack. Further, since the direction of the pressing force of the pressing members inclines relative to a horizontal and vertical surfaces, partial force that presses the part rack 12 downward is generated to prevent the rack 12 from floating.

The third stage corresponds to an open and close state of the movable plates 34a and 34b maintained when the empty part rack 12 from which the parts 13 have been consumed is recovered from the part take-out station B and transferred to the lift 84 of the rack recovering part. At the third stage, the maximum interval is maintained between the pair of movable plates 34a and 34b. This maximum interval is larger than the distance between the opposite ends of the protruding parts 65a and 65b, so that the empty part rack 12 falls onto the lift 84 so as to stack up on already recovered empty racks, the lift 84 having been raised up to a position closer to the part take-out station B than to the lowest position.

Now, an operation performed by the rack recovering part to recover used part racks will be described with reference to FIGS. 3, 4, and 5. At the part take-out station B, the parts are consumed one by one, and when few parts remain on the part rack 12, the lift 84, which has been standing by at the lowest position, is raised to the part take-out station B. Then, when the uppermost position sensor 40 senses the uppermost one of the used part racks already stacked together on the lift 84, the controller 90 stops raising the lift 84. In this case, even if no recovered empty racks are placed on the lift, the uppermost position sensor 40 senses the receiving member 19b, which is substantially as high as the part rack on the lift 84, to similarly stop the lift.

Once the disposable nozzle tips 13a and/or reaction containers 13b on the part rack 12 positioned on the part take-out station B have been used up, the controller 90 controls the operation of the pulse motor 33 of the floor-part opening and closing mechanism 11 to maximize the opening of the pair of movable plates 34b and 34b to drop the used part rack 12 onto the lift 84. That passage through which the part rack falls is limited by the guide wall 35 to fit the outward form of the part rack, so that the part rack falls a short distance while maintaining substantially the same position as that it assumed on the part take-out station, and then sits on the already recovered other part racks or the receiving member 19b. The part rack falls from the part take-out station B to the uppermost position sensor 40. This short falling distance serves to make possible noise low during the fall and to prevent the part rack from being damaged. Further, the part rack can be reliably staked up on the other part racks while maintaining its position.

When the fall detecting sensor 16, arranged in the fall passage, senses that the part rack 12 has fallen, the controller 90 realizes that the part rack has been normally recovered, and lowers the lift 84 down to the lowest position. When the fall detecting sensor 16 does not sense the part rack, the controller 90 lowers the lift 84 down to the lowest position, while determining that an error has occurred during the receiving operation to output a warning notifying the operator of the error, using the buzzer 45 and/or display 44.

When the position sensor 36 detecting the lowest position senses the lift 84, the table 84 is stopped, and on the basis of the number of pulses supplied to the pulse motor 37 and required for this fall, the controller 90 calculates the number of part racks recovered and placed on the lift 84. When the calculated number reaches a preset threshold, the controller 90 outputs a warning using the buzzer 44 and/or display 44 to urge the operator to take out the recovered part racks from the rack recovering part. This configuration enables up to a predetermined number of the used part racks to be recovered in order while being stacked together on the lift, thereby reducing the required volume of the recovering part. Further, the supply lifter 14 is arranged by the side of the recovery lifter 15 to feed unused part racks with unused disposable parts mounted thereon, thereby reducing the required floor area of the part feeding device 80.

The invention claimed is:

1. An automatic analyzer that analyzes samples using parts arranged in part racks, comprising:
 a supply lifter configured to receive a plurality of part racks holding unused parts, said supply lifter being mounted for vertical movement and positioned to raise the part racks to a rack separation station, while keeping the part racks stacked together;
 a rack separator located at the rack separation station able to separate an uppermost part rack of said part racks from remaining said part racks so as to retain the separated uppermost part rack at said rack separation station;
 a recovery lifter positioned to be able to receive the separated part rack following processing, said recovery lifter being mounted for vertical movement to move the separated part rack downward for recovery;
 a laterally movable table having the supply lifter and the recovery lifter mounted thereon;
 a first rack position sensor positioned to sense the uppermost one of the part racks;
 a second rack position sensor positioned to sense a second part rack located under the uppermost one of the part racks in the vicinity of said rack separation station; and
 a controller means for determining whether or not said uppermost part rack has been properly separated from the other part racks on the basis of sensed information received from said first and second rack position sensors, the controller means including means for judging whether to continue operation or interrupt the operation based on determination of whether said uppermost part rack has been properly separated.

2. An automatic analyzer that analyzes samples using parts disposed in part racks, comprising:
 a supply lifter configured to receive a plurality of part racks, said supply lifter being mounted for vertical movement and positioned to raise the plurality of part racks to a rack separation station, while keeping the part racks stacked together;
 a rack separator located at the rack separation station able to separate an uppermost one of the stacked part racks so as to leave the uppermost part rack at the rack separation station;
 plural sensors positioned to sense whether the uppermost part rack has been properly separated from said stacked part racks; and
 a controller means for determining whether to continue operation of the analyzer or interrupt operation of the analyzer based upon information received from said plural sensors.

3. The automatic analyzer according to claim 2, further including
 a laterally moveable table, wherein said supply lifter and said moveable table are housed in an enclosed rack lift chamber, and said movable table is slideably mounted to move out of the rack lift chamber through a door, whereby an operator is able to pull the moveable table out of the rack lift chamber to add part racks holding parts to said supply lifter while said analyzer continues to analyze samples.

4. The automatic analyzer according to claim 2, further including
 a recovery lifter mounted for vertical movement and positioned to receive part racks following use;

a first belt and first motor for controlling the position of the supply lifter, and a second belt and a second motor for controlling the position of the recovery lifter independently of the supply lifter.

5. The automatic analyzer according to claim 2, wherein said supply lifter is mounted on a movable table housed in a rack lift chamber having a door, said door including a lock, wherein said controller means includes means for automatically locking said door while said supply lifter is in operation for preventing access to said rack lift chamber, and wherein said controller means further includes means for unlocking said lock to enable said door to be opened when said supply lifter is in an inactive position, whereby part racks may be added while said analyzer is able to continue to analyze samples.

6. The automatic analyzer according to claim 2, further including an alarm means for notifying an operator when a quantity of part racks remaining on said supply lifter has reached a predetermined minimum quantity threshold, as calculated by said controller means by counting a number of pulses transmitted to a motor controlling said supply lifter when lowering said supply lifter from a highest position to a lowest position.

* * * * *